United States Patent [19]

Sitzmann

[11] Patent Number: 5,183,938
[45] Date of Patent: Feb. 2, 1993

[54] N,N'-BIS(4,4,4-TRINITROBUTYRYL)HYDRAZINE

[75] Inventor: Michael E. Sitzmann, Adelphi, Md.

[73] Assignee: The United States of America as represented by the Secretary of the Navy, Washington, D.C.

[21] Appl. No.: 901,620

[22] Filed: Jun. 15, 1992

[51] Int. Cl.$^5$ .................. C07C 139/08; C06B 47/08
[52] U.S. Cl. .................. 564/151; 149/36; 149/88; 564/143
[58] Field of Search .................. 149/36, 88; 564/143, 564/151

[56] References Cited

U.S. PATENT DOCUMENTS

| | | | |
|---|---|---|---|
| 2,311,098 | 2/1943 | Swan et al. | 564/151 |
| 3,373,181 | 3/1968 | Linden et al. | 149/36 |
| 3,624,129 | 11/1971 | Kamley | 149/88 |
| 3,624,130 | 11/1971 | Klemm et al. | 560/27 |
| 3,894,990 | 7/1975 | Müller et al. | 524/192 |
| 4,659,403 | 4/1987 | Kirschke et al. | 149/36 |
| 4,683,085 | 7/1987 | Frankel et al. | 149/88 |

Primary Examiner—Edward A. Miller
Attorney, Agent, or Firm—Kenneth E. Walden; Roger D. Johnson

[57] ABSTRACT

N,N'-Bis(4,4,4-trinitrobutyryl)hydrazine which is prepared by reacting 4,4,4-trinitrobutyryl chloride with hydrazine in methanol at low temperature. This compound is sensitive enough to be used as an initiating explosive and thermally stable enough to be used in missile warheads.

7 Claims, No Drawings

N,N'-BIS(4,4,4-TRINITROBUTYRYL)HYDRAZINE

BACKGROUND OF THE INVENTION

This invention relates to explosive compounds and more particularly to explosive nitroorganic compounds.

Missile systems often require initiating explosives that can withstand high temperatures (150° C. or higher) generated by aerodynamic heating during the flight of the missile. Many trinitromethyl compounds are known to have sufficient sensitivity to be useful as initiating explosives but extremely few of these materials have melting points and thermal stabilities that would allow their use at temperatures in the vicinity of 150° C. and above. For example, N,N'-bis(2,2,2trinitroethyl)oxamide and N,N'-bis(2,2,2-trinitroethyl)urea have high melting points (210° C. and 188° C., respectively) but their stabilities at temperatures in the vicinity of 150° C. are marginal or inadequate.

Therefore, it would be desirable to provide an explosive that is sensitive enough to be used as an initiating explosive and yet is thermally stable enough to resist the aerodynamic heating recurring during missile flights.

SUMMARY OF THE INVENTION

Accordingly, an object of this invention is to provide a new energetic compound.

Another object of this invention is to provide a new energetic compound that is useful as an initiating explosive.

A further object of this invention is to provide a new energetic explosive that has enough thermal stability to be used in missile warheads.

These and other objects of this invention are accomplished by providing:
N,N'-bis(4,4,4-trinitrobutyryl)hydrazine,
$C(NO_2)_3CH_2CH_2C(=O)NHNHC(=O)CH_2CH_2C(NO_2)_3$.

The N,N'-bis(4,4,4-trinitrobutyryl)hydrazine is prepared by
(1) forming a reaction solution at a temperature of from about $-40°$ C. to about $-90°$ C. by mixing
   (a) a solution of hydrazine dissolved in a lower molecular weight alcohol that is methanol, ethanol, 1-propanol, 2-propanol, 1-butanol, 2-butanol, 2-methyl-1-butanol, or mixtures thereof with
   (b) a solution of 4,4,4-trinitrobutyryl chloride, wherein the mole ratio of hydrazine to 4,4,4-trinitrobutyryl chloride is from about 1.25:1 to about 1.80:1;
(2) placing the reaction solution formed in step (1) into an ambient temperature environment and allowing the reaction mixture to warm up to a temperature of from about $-5°$ C. to about 25° C.; and then
(3) isolating the product N,N'-bis(4,4,4-trinitrobutyryl)hydrazine.

DETAILED DESCRIPTION OF THE PREFERRED EMBODIMENT

A new energetic compound N,N'-bis(4,4,4trinitrobutyryl)hydrazine (I), $C(NO_2)_3CH_2CH_2C(=O)NHNHC(=O)CH_2CH_2(NO_2)_3$, has properties which make it desirable for use as an initiating explosive in missile N,N'-bis(4,4,4-trinitrobutyryl)hydrazine is an initiating explosive with impact sensitivity of 18 cm (RDX =22 cm). N,N'-bis(4,4,4-trinitrobutyryl)hydrazine has a melting point of 201° C. and exhibits excellent short time thermal stability at 150° C. A sample of N,N'-bis(4,4,4-trinitrobutyryl)hydrazine held at 150° C. for one hour showed no evidence of decomposition and no change in melting point.

The N,N'-bis(4,4,4-trinitrobutyryl)hydrazine (I) is prepared by reacting two moles of 4,4,4-trinitrobutyryl chloride (II), $C(NO_2)_3CH_2CH_2C(=O)Cl$, with one mole of hydrazine, $NH_2NH_2$. Trinitromethyl compounds are readily destroyed by hydrazine due to the strongly nucleophilic and reducing properties of this reagent. However, it was found that I (mp 201° C, dec.) can be prepared in high yield (84%) by the addition of a solution of hydrazine in methanol to 4,4,4-trinitrobutyryl chloride (II) in ethyl ether at low temperature:

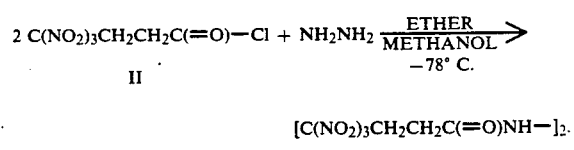

$$2\ C(NO_2)_3CH_2CH_2C(=O)-Cl + NH_2NH_2 \xrightarrow[-78°\ C.]{\text{ETHER}\atop\text{METHANOL}}$$

$$[C(NO_2)_3CH_2CH_2C(=O)NH-]_2.$$

I

The methanol hydrogen bonds with hydrazine to suppress its destructive properties toward trinitromethyl compounds. In general, the hydrazine is dissolved in a suitable solvent that forms hydrogen bonds with hydrazine, has a low melting point, and will not interfer with the reaction. Preferred solvents for the hydrazine include lower molecular weight alcohols such as methanol, ethanol, 1-propanol, 2-propanol, 1-butanol, 2-butanol, 2-methyl-1-propanol, or mixtures thereof, with methanol and ethanol being more preferred, and methanol being most preferred. The solvent used to form the initial 4,4,4-trinitrobutyryl solution must (1) be capable of providing at least some solubility for 4,4,4-trinitrobutyryl chloride, (2) remain a liquid at the process temperatures, and (3) be inert (not interfer with the process reactions). As demonstrated by the example, diethyl ether is an excellent solvent for this purpose. Other common solvents having these properties, such as dichloromethane, may also be used.

Low temperatures also reduce side reactions with hydrazine as well as the reaction of the acid chloride with methanol Therefore the hydrazine solution and the 4,4,4-trinitrobutyryl chloride solution are mixed together at a temperature in the range of preferably about $-40°$ C. to $-100°$ C., more preferably from $-60°$ C. to $-90°$ C., and still more preferably from $-70°$ C. to $-85°$ C., with about $-78°$ C. being most preferred. The resulting reaction solution is then put in ambient (room) temperature environment and allowed to warm up to a temperature in the range of from about $-5°$ C. to about 25° C. The product N,N'-bis(4,4,4-trinitrobutyryl)hydrazine is then isolated using conventional techniques as illustrated in the example.

From the reaction above it would appear that the molar ratio of hydrazine to 4,4,4-trinitrobutyryl chloride should be 0.5:1. However, the reaction generates HCl which will reduce the yield if it is not removed. Therefore, an excess of hydrazine is used to complex with and remove the HCl from the reaction solution. As a result, the molar ratio of hydrazine to 4,4,4-trinitrobutyryl chloride is preferably from about 1 25:1 to about 1.80:1 and more preferably from 1.40:1 to 1.80:1. Using more hydrazine is undesirable because the extra hydrazine is not needed and will attack the trinitromethyl groups Using less than the preferred amount of hydrazine will reduce the yield.

To more clearly illustrate this invention, the following example is presented. It should be understood, however, that this example is presented merely as a means of illustration and is not intended to limit the scope of the invention in any way.

EXAMPLE

N,N'-Bis (4,4,4-trinitrobutyryl)hydrazine (I)

A solution of 3.0 g (0.0124 mole) of 4,4,4-trinitrobutyryl chloride in 15 ml of diethyl ether was stirred at $-78°$ C. (dry ice-acetone bath) during the dropwise addition of a solution containing 0.7 g (0.0218 mole) of hydrazine (95% minimum) in 15 ml of methanol. The reaction mixture was allowed to warm to 0° C. over 10 minutes. The mixture was poured into water (60 ml) and the ether was evaporated to give an insoluble white solid which was removed by filtration and washed with water. The melting point (201° C.) of the solid (2.3 g, 84%) was not raised by crystallization from 1,2-cichloroethane; $^1$H NMR (acetone $d_6+D_2O$): 2.90(m, 2H), 3.80(m, 2H); IR(KBr): 3240(NH), 1700(shoulder), 1640 (C=O), 1600 (NO2). Anal. Calcd for $C_8H_{10}N_8O_1$: C, 21.73; H, 2.28, N, 25.34. Found C, 22.05; H, 2.21; N, 25.24.

The 4,4,4-trinitrobutyryl chloride (Chemical Abstract Number 36638-86-5) starting material was prepared by refluxing 4,4,4-trinitrobutyric acid with an excess of thionyl chloride for 20 hours before the mixture was concentrated in vacuo and the product distilled as taught by Marvin H. Gold, et al. in an article titled, "Preparation of Aliphatic gem-Dinitro Monoisocyanates and Derivatives," *Journal of Organic Chemistry* (1962), volume 27, pages 334-335, at page 334, column 2, herein incorporated by reference in its entirety.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. N,N'-bis(4,4,4-trinitrobutyryl)hydrazine.

2. A process for preparing N,N'-bis(4,4,4-trinitrobutyryl)hydrazine comprising:
   (1) forming a reaction solution at a temperature of from about -40° C. to about -90° C. by mixing
      (a) a solution of hydrazine dissolved in a lower molecular weight alcohol that is methanol, ethanol, 1-propanol, 2-propanol, 1-butanol, 2-butanol, 2-methyl-1-butanol, or mixtures thereof with
      (b) a solution of 4,4,4-trinitrobutyryl chloride, wherein the mole ratio of hydrazine to 4,4,4-trinitrobutyryl chloride is from about 1.25:1 to about 1.80:1;
   (2) placing the reaction solution formed in step (1) into an ambient temperature environment and allowing the reaction mixture to warm up to a temperature of from about $-5°$ C. to about 25° C.; and then
   (3) isolating the product N,N'-bis(4,4,4-trinitrobutyryl)hydrazine.

3. The process of claim 2 wherein the mole ratio of hydrazine to 4,4,4-trinitrobutyryl chloride is from 1.40:1 to 1 80:1.

4. The process of claim 2 wherein the lower molecular weight alcohol is methanol or ethanol.

5. The process of claim 4 wherein the lower molecular weight alcohol is methanol.

6. The process of claim 2 wherein the temperature in step (1) is from $-60°$ C. to $-90°$ C.

7. The process of claim 6 wherein the temperature in step (1) is from $-70°$ C. to $-85°$ C.

* * * * *